United States Patent [19]

DeMarco

[11] 4,353,362
[45] Oct. 12, 1982

[54] KNEE BRACES

[76] Inventor: Alexander H. DeMarco, 85 Maple Ave., Shelton, Conn. 06484

[21] Appl. No.: 260,021

[22] Filed: May 4, 1981

[51] Int. Cl.³ .............................................. A61F 3/00
[52] U.S. Cl. ................................................ 128/80 C
[58] Field of Search ............... 128/80 C, 87 R, 165, 128/DIG. 15; 2/22, 24

[56] References Cited

U.S. PATENT DOCUMENTS

| | | | |
|---|---|---|---|
| 3,804,084 | 4/1974 | Lehman | 128/80 C |
| 3,831,467 | 8/1974 | Moore | 128/80 C |
| 3,935,858 | 2/1976 | Harroff | 128/165 |
| 4,296,744 | 10/1981 | Palumbo | 128/80 C |

*Primary Examiner*—John D. Yasko
*Attorney, Agent, or Firm*—Walter Spruegel

[57] ABSTRACT

Knee brace of unfolding type has a wrap-on pad with quick-fasteners on opposite sides for initial pad application to a knee, and tapes for finish application of the pad to the knee, with the pad also having stays to lend it rigidity over part of its knee-enveloping expanse while permitting ready natural flexure of the braced knee.

1 Claim, 6 Drawing Figures

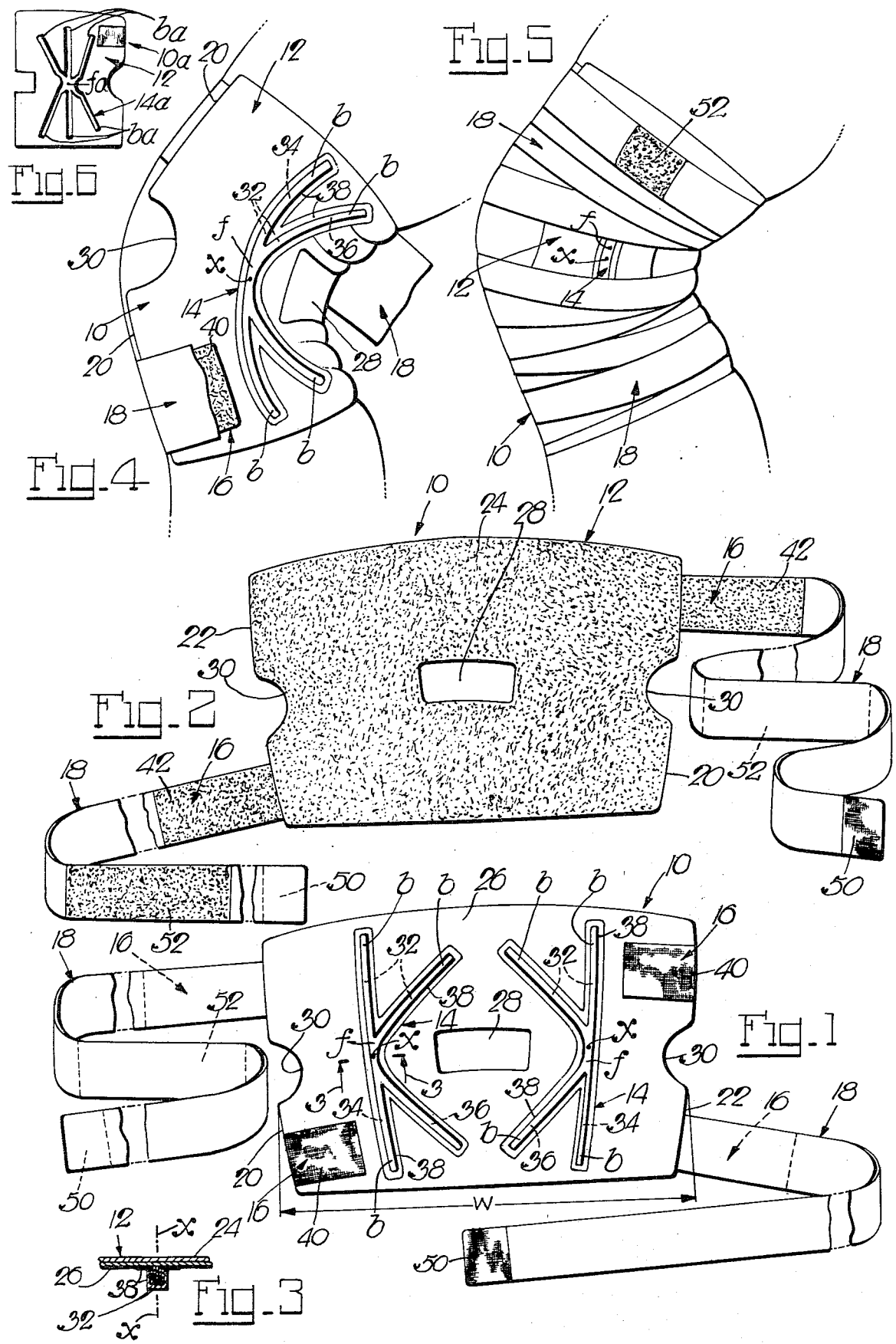

KNEE BRACES

This invention relates to knee supports in general, and to knee braces in particular.

The knee is known to be one of the joints of the human body which is all too easily subjected to severe stresses and strain owing to the distribution over its small area of the heavy body weight which it must bear, coupled with its diverse movements within the narrow confines of its natural flexion in the course of one's accustomed activies. It is thus no wonder that knees are all too easily injured often as the result of being abnormally bent in sports and other strenuous activities, or in falls or other accidents, and they also become weak as in advanced age or from crippling decease, such as arthritis, for example. To protect knees against injury from these and other causes and also lend them adequate support when weak from any cause or in various srages of convalescence, recourse is frequently had to knee braces which are essentially pads that are slipped over or wrapped around knees and are often provided with stays that permit bending of the knees in natural flexion but resist most other bending.

The present invention is concerned with knee braces of unfolding type which are wrapped around the knees, thereby to leave their bind to the knees for comfortable and/or other beneficial wear to the discretion of the user or judgement of a professional attendant. However, while prior knee braces of this type are satisfactory in most respects, they fall short of being satisfactory in a few other respects. Thus, such prior braces customarily have Velcro or other fasteners for holding the braces on the knees to which they are applied, but their hold on the knees by the expediency of such fasteners, if not prohibitively tight, is not sufficiently secure to prevent their slipping or other disarrangement on the knees particularly on repeated bending of the knees in ordinary use, neither do such local fasteners bind the braces to the knees with sufficient uniformity throughout to hold them with the same even snugness, and hence also feel, against the knees in their various dispositions in repose and action.

It is among the objects of the present invention to provide knee braces of unfolding type which in their application are bound to knees, not only with the necessary firmness to prevent their slipping or other disarrangement in accustomed use, including bending, but also with sufficient uniformity throughout to hold them with the same even snugness, and hence also feel, against the knees in their various dispositions. To this end, the braces rely on, and feature, taping for their hold on knees, with the tapes being provided advantageously directly on the braces, and being wound around the applied braces in sufficient and well-placed turns and at the right tension to hold the braces in secure and uniform fit with the knees in their various dispositions.

It is another object of the present invention to provide knee braces of unfolding type which, in addition to the aforementioned tapes for their secure and even hold on knees, also provide, and further feature, quick-fasteners for initial easy and instantaneous application of the braces to knees in the right location and disposition thereon, thereby greatly to facilitate the task of correct initial brace application especially, though not exclusively, by the user himself or herself, and also facilitate the task of finish-winding the tapes on the initially applied braces in evenly distributed turns and at the correct tension by the user or by an attendant with both of his or her hands.

Another object of the present invention is to provide knee braces of unfolding type with the aforementioned wind-on tapes and quick-fasteners, of which the fasteners are of preferred Velcro type with the customary companion hook and loop pads, of which half of the pads are secured to a brace along one side thereof, and their associated pads are secured to the tapes locationwise and extentwise thereon so that the companion pads will be within locking reach of each other when the tapes surround the initially applied brace on a knee anywhere within a fraction, and preferably less than half, of a turn. With this arrangement, braces of a given or standard size are initially applied to knees not only easily and instantaneously, but also with any desired fit or snugness regardless of even fairly wide differences in the size of the knees.

A further object of the present invention is to provide knee braces of unfolding type which are equipped with stays that are arranged to keep the applied braces fairly rigid, not just locally on opposite sides, but over an extensive part, of their envelopment of the knees so that they effectively prop, and also largely absorb potentially damaging blows or other forces against, the knees, without, howver, interfering with their natural flexion. To this end, the stays are secured to a brace so that they extend in groups on opposite sides, respectively, of the knee to which the brace is applied, with the stays of each group being gathered together and arranged intermediate their lengths at a location of the brace to form a fulcrum about which the stays will readily flex on natural flexing of the knee, and the stays of each group diverging from their fulcrum formation to span the contemplated part of the brace's envelopment of the knee and thereby lend the desired rigidity to this part of the brace.

Further objects and advantages will appear to those skilled in the art from the following, considered in conjunction with the accompanying drawings.

In the accompanying drawings, in which certain modes of carrying out the present invention are shown for illustrative purposes:

FIG. 1 is a front view of a knee brace embodying the invention;

FIG. 2 is a rear view of the same knee brace;

FIG. 3 is an enlarged fragmentary section through the knee brace as taken on the line 3—3 of FIG. 1;

FIG. 4 is a perspective view of the knee brace as partly applied;

FIG. 5 is another perspective view of the knee brace in fully applied condition; and FIG. 6 is a fragmentary front view of a modified knee brace.

Referring to the drawings, and more particularly to FIGS. 1 to 5 thereof, the reference numeral 10 designates a knee brace of unfolding type which has as its major elements a pad 12 with stay assemblies 14, quick-fasteners 16 and tapes 18.

The pad 12, which is usually unfolded when not in use (FIGS. 1 and 2), is generally trapezoidal in outline, having opposite sides 20 and 22 and being of a width w therebetween to envelope at least most, but preferably not all, of a knee when applied thereto with its sides 20,22 foremost (FIG. 4). The pad 12, which preferably has some resiliency for comfortable wear and good fit properties, is in this instance formed of inner and outer plies 24 and 26, of which the inner ply 24 is to be worn on the user's skin and is of preferred knot or woven terry-like material which is soft and feels comfortable on the skin, while the outer ply is in this instance of a woven resilient material of good wear qualities which is preferably coated with latex for a purpose explained hereinafter as well as for advantageously bonding the outer ply to the inner ply. The pad 12 is also tailored with a central aperture 28 and opposite side recesses 30 which afford the applied pad freedom to bend with the knee without appreciably resisting such bending or becoming overly wrinkled (FIG. 4).

The stay assemblies 14 number two in this instance, and they are located on the pad on opposite sides of a knee on which the pad is worn (FIGS. 1 and 4). Each of these assemblies 14 provides a plurality of stays 32 in the preferred form of flat strips of a suitable material, preferably plastic which has some resiliency, with these strips being divided into two groups 34 and 36 which intermediate their lengths are joined side-by-side to form a fulcrum f with an axis x about which the strips may flex quite freely (FIGS. 1 and 3 to 5). The strips 32 of the groups 34 and 36 diverge from each other beyond their common fulcrum f to simulate in this instance the letter K, and the strips of both groups 34 and 36 are retained in pockets that are formed by bands 38 which are suitably secured in this instance to the outer ply 26 of the pad 12. The stay assemblies 14, while generally provided on the pad 12 on opposite sides of a knee on which the pad is worn, are further located on the pad 12 so that the axes x of their fulcrum formations f lie sufficiently close to the axis of natural flexion of the knee to bend with the latter quite freely (FIGS. 4 and 5), while the diverging parts of the stay assemblies beyond their fulcrum formations f stiffen the pad over their considerable widthwise expanse thereon sufficiently so as largely to absorb and render harmless blows or other forces against the braced knee which otherwise might well cause injury to the knee.

The quick-fasteners 16 are for the purpose of instantaneous initial application of the brace in correct location on a knee so as to free both hands of the wearer of the brace or of an attendant for subsequent finish-application of the brace to the knee by means of the tapes 18. The quick-fasteners 16 number two in this instance, each being of preferred Velcro type and providing two characteristic hook and loop companion parts 40 and 42, of which the hook parts 40 are in this instance secured to the outer ply 26 of the pad 12 on opposite sides of the same (FIG. 1), while the loop parts 42 are suitably secured to the respective tapes 18 next to the pad 12 and on the sides thereof which in their prescribed wind on the applied brace lie next to the latter (FIG. 2). Thus, in placing the pad 12 on a knee in correct location thereon as in FIG. 4, it is merely necessary for initial and sufficiently secure hold of the pad on the knee to start winding the tapes 18 on the braced knee for a mere fraction of a turn, i.e., just sufficiently to bring the loop fastener parts 42 on the tapes into overlap with their companion hook parts 40 so that these fastener parts 40, 42 interlock on their mere engagement, as will be readily understood.

The tapes 18 also number two, and they are suitably secured to the pad 12 and extend from the opposite sides 20 and 22 thereof. These tapes 18 are preferably of any suitable woven and preferably somewhat resilient material, and they are of considerable length so that each may be wound on the initially applied brace on a knee in a good number of turns (FIG. 5) which may be spaced fairly evenly and applied with the right snugness for comfortable and/or other beneficial wear of the brace and for rather free natural bending of the braced knee, as well as for retention of the wound tapes in good fit with the braced knee in all accustomed activities of the same. In this connection, the preferred latex-coated outer ply 26 of the pad 12 contributes toward a good bind of the wound tapes to the applied pad on the knee and, hence, to retention of these tapes in good and secure fit with the braced knee in all accustomed activities, including natural bending, of the latter.

The tapes 18 are also provided with preferred Velcro fasteners for holding the wound tapes from unwinding, with each fastener providing characteristic hook and loop parts 50 and 52, of which the hook parts 50 are provided at the very ends of the tapes and on one side thereof, while their companion loop parts 52 are provided on the opposite sides of the tapes and spaced from their associated hook parts 50, with the companion hook and loop fastener parts 50 and 52 on each tape being of sufficient extent lengthwise of the latter and so spaced that these fastener parts will come into overlap and on engagement securely interlock with each other on the last turn of the tape around a braced knee of most any size. Similarly, the hook and loop companion fastener parts 40 and 42 for the described instantaneous initial hold of the brace on a knee are of sufficient extent, widthwise of the pad 12, to come into overlap for their interlock on engagement with each other on winding the tapes for no more than a fraction, and mostly for much less than half, of a turn around the pad when applied to a knee of most any size.

While the described knee brace 10 of FIGS. 1 to 5 provides stay assemblies 14 which have two diverging branches b on each side of their fulcrum formations f, FIG. 6 shows a modified knee brace 10a which may in all respects be like the brace 10, except that the stay assemblies 14a have more than two, and in this instance three, diverting branches ba on each side of their fulcrum formations fa to thus stiffen the pad 12a over wider parts of its width.

What is claimed is:

1. A knee brace of unfolding type, providing a resilient pad having front and back faces and opposite sides and being of a width for partial envelopment of knees of different circumferences when applied thereto, and being of a given length for extension above and below a knee, two tapes extending from said pad and being of sufficient length for winding a plurality of times around said pad when in enveloping relation with a knee, said tapes have free ends and extend from lengthwise spaced parts of the opposite sides, respectively, two Velcro fasteners each having first and second companion parts on said front face of said pad along one side thereof and on an associated tape extending from the other associated pad side, respectively, with said companion fastener parts releasably interlocking when engaged with each othe, and each of said second fastener parts extending on the associated tape from the associated pad side outwardly sufficiently to be engageable with its companion fastener part on bridging the gap between the sides of the applied pad on a knee on wind-on of the tape for a fraction of one turn and said first fastener parts are arranged along said pad sides, respectively, and are aligned, widthwise of said pad, with the lengthwise spaced parts of the pad sides from which extend the tapes that carry the respective companion fastener parts so as to indicate wind-on of the tapes on the applied pad in opposite directions, and a further Velcro fastener on each tape having companion parts at, and so spaced from, the end of the tape to be engageable with each other on the last turn of the wind-on of the tape.

* * * * *